United States Patent
Roos et al.

(10) Patent No.: US 9,414,965 B2
(45) Date of Patent: Aug. 16, 2016

(54) HEIGHT ADJUSTMENT ARRANGEMENT FOR AN EAR CUP IN A HEARING PROTECTOR UNIT

(75) Inventors: Anders Roos, Varnamo (SE); Thomas Isaksson, Varnamo (SE)

(73) Assignee: MSA SORDIN AB, Varnamo (SE)

( * ) Notice: Subject to any disclaimer, the term of this patent is extended or adjusted under 35 U.S.C. 154(b) by 458 days.

(21) Appl. No.: 13/994,044

(22) PCT Filed: Oct. 7, 2011

(86) PCT No.: PCT/SE2011/051210
§ 371 (c)(1),
(2), (4) Date: Sep. 6, 2013

(87) PCT Pub. No.: WO2012/082047
PCT Pub. Date: Jun. 21, 2012

(65) Prior Publication Data
US 2013/0340769 A1    Dec. 26, 2013

(30) Foreign Application Priority Data
Dec. 14, 2010 (SE) ...................... 1051313

(51) Int. Cl.
*A61F 11/14* (2006.01)
*H04R 1/10* (2006.01)

(52) U.S. Cl.
CPC ............... *A61F 11/14* (2013.01); *H04R 1/1066* (2013.01); *H04R 2460/17* (2013.01)

(58) Field of Classification Search
CPC ..................................................... A61F 11/14
USPC .......... 2/426, 422, 423, 417, 419, 6.3, 13, 15, 2/10, 209; 381/374, 376–379, 370, 381, 381/383
See application file for complete search history.

(56) References Cited

U.S. PATENT DOCUMENTS

| | | | | |
|---|---|---|---|---|
| 1,329,658 A | * | 2/1920 | Gernsback | 381/379 |
| 1,555,997 A | * | 10/1925 | Lidberg | 381/378 |
| 1,570,129 A | * | 1/1926 | Clarke | 379/430 |
| 2,717,930 A | | 9/1955 | Hintz | |
| 4,756,028 A | | 7/1988 | Scanlon | |

FOREIGN PATENT DOCUMENTS

GB    1347824 A    2/1974

OTHER PUBLICATIONS

International Search Authority, Search Report for International Application PCT/SE2011/051210, Mar. 21, 2012 (SE), 1 page.

* cited by examiner

*Primary Examiner* — Nicholas Woodall
*Assistant Examiner* — Tarla Patel
(74) *Attorney, Agent, or Firm* — Ference & Associates LLC

(57) ABSTRACT

The present disclosure relates to a height adjustment arrangement (100) for an ear cup in a hearing protector unit, wherein the height adjustment arrangement (100) comprises an elongated member (130) and a tubular holding member (110) connected to the elongated member, wherein the holding member provides a substantially hollow interior (111). The height adjustment arrangement further comprises a clamping member (120), wherein the clamping member is arranged to be moved from an unlocked position, in which position relative movement between the elongated member (130) and the holding member (110) is enabled, to a locking position, in which position relative movement between the elongated member and the holding member is prevented. The holding member (110) comprises a first locking member (114), wherein the second end of the holding member is provided with two flanges (115a, 115b) tapering in a direction towards the clamping member, and wherein the first locking member and the flanges are axially separated. The clamping member comprises a hollow interior with a tapering part, which tapers in a direction away from the holding member, and a second locking member, wherein the tapering part and the second locking member are axially separated.

19 Claims, 4 Drawing Sheets

HEIGHT ADJUSTMENT ARRANGEMENT FOR AN EAR CUP IN A HEARING PROTECTOR UNIT

TECHNICAL FIELD

The present disclosure relates to a height adjustment arrangement for an ear cup in a hearing protector unit, and especially to an arrangement related to the locking of an ear cup in a certain height position.

BACKGROUND

Ear cups are normally used in hearing protector units. Two ear cups may be connected via a connection unit to a head band to form a hearing protector unit, or be connected via a connection unit to a helmet to form a helmet including a hearing protector unit. For the hearing protector unit to function properly, the ear cups should be placed at a certain location over the user's ears. Due to different head shapes of different users, the ear cups need to be adjustable in height relative to the head band or helmet. Even a small misplacement of the ear cup over the user's ear may provide a significant loss in the sound-attenuating function of the hearing protector unit.

A known way of solving the problem of height adjustment to ear cups in hearing protector units is to provide the connection unit as a height adjustment arrangement comprising a steel wire that is connected to an ear cup via a plastic and/or rubber holder. The holder is designed to provide a friction force between the steel wire and the holder. A user may pull or push the ear cup to a desired height with a force larger than the friction force. When the ear cup is pulled or pushed to the desired height, the friction force between the parts in the height adjustment arrangement will hold the ear cup at that height during use of the hearing protector unit.

A problem with such height adjustment arrangement for an ear cup in a hearing protector unit is that the parts in the height adjustment arrangement, i.e. the holder and the steel wire, may be worn out over time such that the friction force will be reduced. When the friction force becomes reduced, the ear cups in the hearing protector unit will eventually drop to maximum extended position of the height adjustment arrangement, irrespectively which height of the ear cups the user tries to set. I.e. the friction force trying to hold the ear cup at a certain height becomes less than the force of gravity provided by the ear cup. Thereby, the ear cups are not correctly positioned at the user's ears, resulting in that the sound-attenuating function of the hearing protector unit will be significantly impaired. This problem may be extra significant for electronic hearing protector units which contain heavy batteries that may increase the force of gravity reverse of the friction force during use of the hearing protector unit. Further, such problem will make the hearing protector unit very uncomfortable for the user due to the unsatisfactory fit. The same problem may be caused by differences in production tolerances of the steel wire and the holder. A small difference in the thickness of steel wires for such height adjustment arrangements would cause different friction forces between a steel wire and a holder. Therefore, a very small tolerance in the steel wire diameter is needed to secure a correct friction force when arranged to the holder.

U.S. Pat. No. 1,329,658 discloses a telephone headband hearing unit with a connection unit that may be used in a hearing protector unit. The connection unit comprises a holder with a hollow interior for receiving a part from the head band. The connection unit further comprises a nut cap adapted to integrate with the holder. The holder and the nut cap each comprises a tapering part, in a truncated cone shape, provided with threads to integrate with each other. Such solution alleviates some of the problems above with friction dependency. However, the solution in U.S. Pat. No. 1,329,658 has a problem in that the connection between the holder and the nut cap may be insecure.

Consequently, there is a need for a height adjustment arrangement for the ear cups in a hearing protector unit that provides a reliable and secure solution over long time use.

SUMMARY

It is an object of the present invention to provide an improved solution that alleviates the mentioned drawbacks with present devices. Furthermore, it is an object to provide a height adjustment arrangement for an ear cup in a hearing protector unit that is not sensitive to wear of the parts in the arrangement.

According to a first aspect of the invention, this is achieved by a height adjustment arrangement for an ear cup in a hearing protector unit, wherein the height adjustment arrangement comprises an elongated member adapted to be coupled in a first end to a head mounting portion of a hearing protector unit, and a tubular holding member connected to the elongated member, the tubular holding member being adapted to be coupled in a first end to an ear cup, wherein the holding member provides a substantially hollow interior adapted to receive a second end of the elongated member. A relative movement between the elongated member and the holding member provides a height adjustment of an ear cup relative to a head mounting portion. The height adjustment arrangement further comprises a clamping member, wherein the clamping member is arranged to be moved from an unlocked position, in which position relative movement between the elongated member and the holding member is enabled, to a locking position, in which position relative movement between the elongated member and the holding member is prevented. The clamping member is further adapted to, when in the locking position, be attached to the holding member such that the clamping member presses a second end of the holding member towards the elongated member to prevent relative movement between the elongated member and the holding member. The holding member comprises a first locking member, wherein the second end of the holding member is provided with two flanges tapering in a direction towards the clamping member, and wherein the first locking member and the flanges are axially separated. The clamping member comprises a hollow interior with a tapering part, which tapers in a direction away from the holding member, and a second locking member, wherein the tapering part and the second locking member are axially separated. When the clamping member is moved from said unlocked position to said locking position, the second locking member is arranged to integrate with the first locking member and the tapering part is arranged to press the flanges towards the elongated member.

Since the clamping member may prevent the relative movement between the holding member and the elongated member in a locking position, and enable the same movement in an unlocked position, the arrangement may not be sensitive to wear of the parts in the arrangement. Contrary the prior art solution wherein the arrangement both enables relative movement of the parts, and holds the parts in a set position at the same time, only a little wear to the parts would cause the arrangement to lose the function of holding the parts in a set position. When the clamping member is in the unlocked position, the holder may be moved relative to the elongated member. Thereby the ear cup may be moved relative to the elongated member and the head mounting portion. When a wanted position of the holder and ear cup relative to the elongated member is reached, the clamping member may be moved to the locking position. Thereby, the set position of the holder and ear cup is fixed relative the elongated member. A head mounting portion may be a headband connected to the height adjustment arrangement. The head mounting portion may alternatively be a helmet or the like, adapted to be worn by a user, and connected to the height adjustment arrangement. Further, with an arrangement according to the invention, larger tolerances for the elongated member diameter may be possible, since two different positions of the clamping member enables or prevents the movement between the elongated member and the holding member. The elongated member may be a wire member, such as a steel wire.

By pressing an end portion of the holding member against the elongated member the friction between the holding member and the elongated member may be increased to a level such that the relative movement between the two members is prevented. A friction force between the holding member and the elongated member that is much larger than the gravity force by the ear cups may prevent the gravity force for affecting the position of the holding member relative to the elongated member. The friction force may be of an amount such that a user cannot move the holder relative to the elongated member by hand.

When the clamping member is moved from the unlocked position towards the locking position, there may be a gradual pressing action by the clamping member on the holding member. The tapering inner surface of the clamping member may provide that the holding member is pressed harder towards the elongated member the further towards the locking position the clamping member is moved.

When the flanges of the holding member tapers in a direction towards the clamping member, a more even gradual pressing action by the clamping member on the flanges may be achieved. The flanges may taper towards the end of the holding member.

By providing a locking member on each of the holding member and the clamping member, the clamping member may be kept in the locking position by means of the locking members integrating with each other. When securing that the clamping member is kept in the locking position, the friction force in the locking position may be secured. Thereby, the set position of the holding member relative to the elongated member may be kept. Further, by unlocking the locking members from each other, the clamping member may be moved from the locking position. Thereby, the clamping member may be moved to the unlocked position such that the holding member may be moved relative to the elongated member. The first locking member and the second locking member may be separated from each other when the clamping member is in the unlocked position. By having the tapering flanges and the first locking member, as well as the tapering part and the second locking member, axially separated, the locking members may be provided in a shape that enables a secure and robust integration. Locking members that are provided on tapering parts may suffer from being insecure and may be loose, especially during integration when the clamping member is moved towards the locking position. The integration between locking members may further in such case be unstable due to flexibility in the flanges. Axially separated locking members and tapering part/flanges may result in non-tapering locking members. The locking members may be provided on a straight portion of the holding member and the interior of the clamping member respectively. This may provide a secure integration between the locking members.

In a further embodiment, the amount of force with which the clamping member may press the second end of the holding member towards the elongated member may be adjustable.

Thereby, the friction force between the holding member and the elongated member may be adjustable. A continuous movement from the unlocked position to the locking position may be achieved. By achieving a continuous adjustment of the friction force, a position of the clamping member may be possible wherein relative movement between the holding member and the elongated member is enabled at the same time as the holding member may be held in a set position by the set friction force. The friction force is thereby larger than the gravity force, but a user may move the holding member relative to the elongated member by overriding the friction force. If the holding member and/or the elongated member may be worn out such that the friction force is reduced, the clamping member may, due to the continuous adjustability, be adjusted such that the friction force may be increased again.

In another embodiment, the holding member may be provided with at least one slit at the second end of the holding member.

A slit at the end of the tubular shaped holding member may provide that the circumference of the holding member may be flexible and may be compressed. Thereby, a larger friction force may be achieved when the clamping member presses the end of the holding member towards the elongated member.

In a further embodiment, the holding member may be provided with two slits at the second end of the holding member.

Thereby, the circumference of the holding member may become even more flexible and may easier be compressed when being pressed against the elongated member. A larger friction force may thereby be achieved by the clamping member pressing the holding member towards the elongated member.

In one embodiment, the two slits may provide two flanges at the second end of the holding member, wherein the clamping member may be adapted to, in the locking position, be attached to the holding member such that the clamping member may press the two flanges at the second end of the holding member towards the elongated member to prevent movement of the elongated member relative to the holding member.

Due to the slits, the flanges may be flexible such that they may be movable in a radial direction of the holding member. Thereby, the clamping member may press the flanges towards the elongated member to prevent the relative movement between the holding member and the elongated member. The elongated member may extend between the two flanges.

In a further embodiment, the clamping member may radially press the holding member towards the elongated member.

The elongated member extending through the tubular holding member may be prevented from movement relative the holding member when the holding member may be radially pressed towards the elongated member. The holding member may be resilient such that it may be pressed radially towards the elongated member.

In another embodiment, the clamping member may be arranged to, when moved from the unlocked position to the locking position, move along an axial direction of the elongated member.

The clamping member may be coaxial with the elongated member. The clamping member may thereby move along the extension of the elongated member when moving between the unlocked position and the locking position. The clamping member may further be coaxial with the holding member and move along an axial direction of the holding member when moving from the unlocked position to the locking position.

In a further embodiment, the first locking member may be outer threads on the holding member and the second locking member may be inner threads in an interior of the clamping member, said outer and inner threads may be adapted for thread engagement with each other.

When moving the clamping member from the unlocked position to the locking position, the inner and outer threads may engage along with the clamping member moving along the axial direction of the elongated member. The clamping member may thereby be screwed onto the holding member, pressing the holding member radially towards the elongated member. The clamping member may be screwed onto the holding member until it locks the clamping member in the locking position. By unscrewing the clamping member from the holding member, releasing the threaded engagement between the locking members, the clamping member may be moved to the unlocked position, enabling relative movement between the holding member and the elongated member.

In a yet further embodiment, the pressing force by the clamping member on the second end of the holding member towards the elongated member may be adapted to increase along with an increased threaded engagement between the clamping member and the holding member.

By screwing the clamping member onto the holding member, the friction force between the holding member and the elongated member may increase until a friction force needed for preventing relative movement between the holding member and the elongated member is reached. If either of the holding member and/or the elongated member would be worn out, the threaded engagement between the clamping member and the holding member may be tightened to compensate for the wear. An adjustable friction force may thereby be provided by the threaded engagement of the locking members. The further the clamping member may be screwed onto the holding member, the harder the holding member may be pressed towards the elongated member. The adjustable friction force may further be used for compensating for a high tolerance in elongated member diameter.

In another embodiment, the first and second locking members together form a bayonet coupling.

The clamping member may thereby in an alternative way be locked to the holding member in the locking position. The clamping member and the holding member may respectively be provided with corresponding parts of a bayonet coupling. The bayonet coupling may be released to be able to move the clamping member to the unlocked position.

According to a second aspect of the invention, a hearing protector unit may be provided comprising at least one ear cup, a head mounting portion and at least one height adjustment arrangement for said ear cup according to any of the claims 1-14. The height adjustment arrangement may be connected with a first end to the head mounting portion and with a second end to the at least one ear cup.

A hearing protector unit may thereby be achieved wherein the ear cup may be adjusted in height relative to the head mounting portion to a position most suitable for a user. The ear cup may be held in that position in a secure way.

BRIEF DESCRIPTION OF THE DRAWINGS

The invention will in the following be described in more detail with reference to the enclosed drawings, wherein.

DESCRIPTION OF EMBODIMENTS

Figure 1:
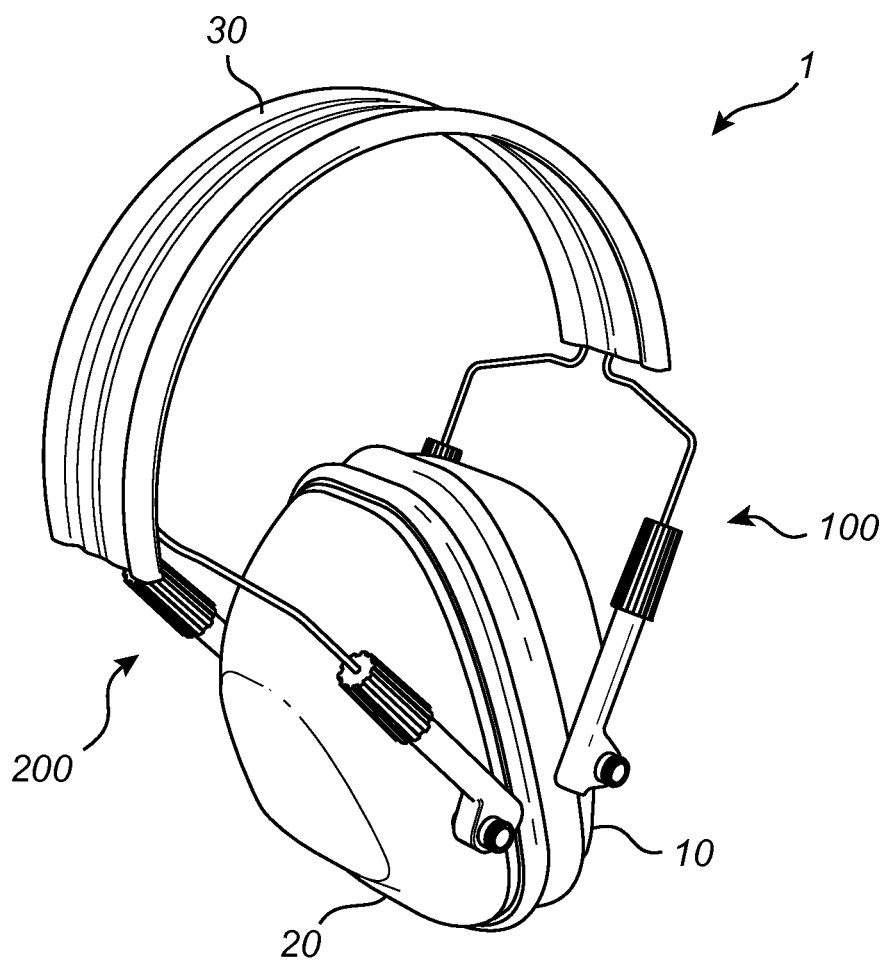
FIG. 1 is a perspective view of a hearing protector unit according to an embodiment of the invention.

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

FIG. 1 illustrates a hearing protector unit 1 adapted to attenuate sound when put on a user's head and over a user's ears. The hearing protector unit 1 comprises two ear cups 10, 20 adapted to be located over the user's ears. A correct placement of the ear cups 10, 20 is crucial for achieving the best sound-attenuating function by the ear cups 10, 20. The ear cups 10, 20 are coupled to each other via a head band 30. The head band 30 is adapted to be placed on the user's head. In an alternative embodiment, the ear cups 10, 20 could be coupled to a helmet. Between the headband 30 and each ear cup 10, 20 there is a height adjustment arrangement 100, 200 provided. Since it is important that the ear cups 10, 20 are placed in a correct way over the user's ears, the ear cups 10, 20 need to be adjustable in height relative to the headband 30. Each height adjustment arrangement 100, 200 is in one end connected to an ear cup 10, 20, and in another end connected to the headband 30.

Figure 2:
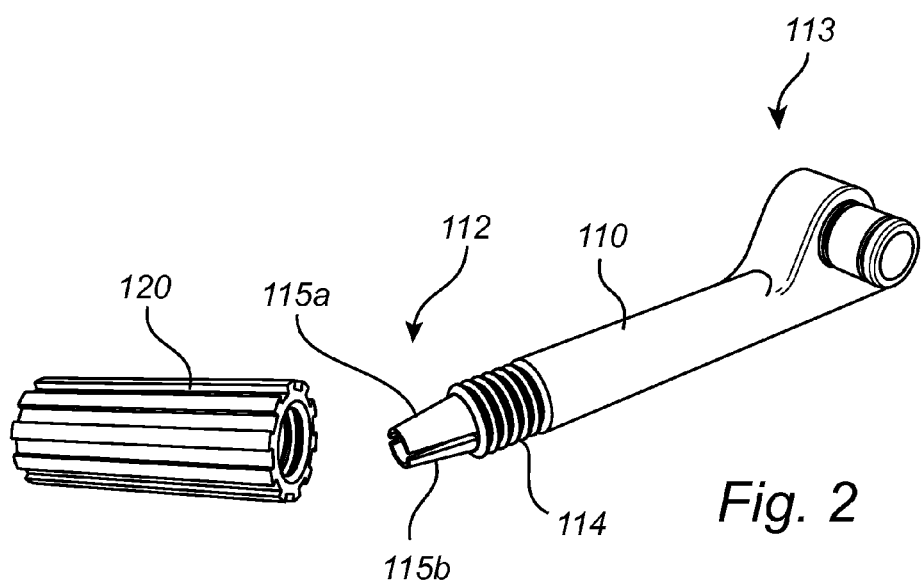
FIG. 2 is a perspective view of a holder and a nut cap according to an embodiment of the invention.
Figure 3A:
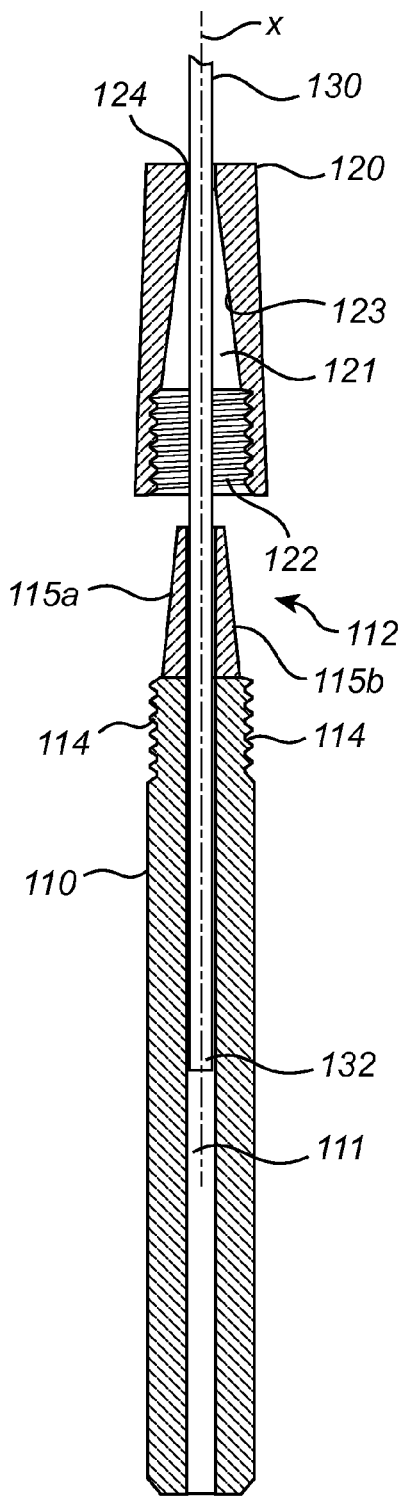
FIG. 3a is a cross-sectional schematic side view of a height adjustment arrangement according to an embodiment of the invention.

The height adjustment arrangement 100 comprises, as illustrated in FIGS. 2 and 3a, a holder 110, a nut cap 120 and a steel wire 130. The holder 110 is tubular and has a hollow interior 111 that is adapted to receive a second end 132 of the steel wire 130. At a second end 112 of the holder 110, there are two slits extending in the longitudinal extension direction of the holder, which is the same as the longitudinal direction of the steel wire 130. The two slits thereby form two flanges 115a, 115b. The flanges 115a, 115b are flexible in a radial direction. Below the flanges 115a, 115b at the second end 112 of the holder 110, there is a first locking member 114, axially separated from the flanges 115a, 115b. The first locking member 114 is provided on a straight, non-tapering part of the holder 110. In the illustrated embodiment, the first locking member 114 is in the form of outer threads. At a first end 113 of the holder 110, the holder 110 is adapted to be connected to an ear cup 10.

The nut cap 120 is provided with an opening 124 at one end adapted to receive the steel wire 130 into a hollow interior 121 of the nut cap 120. The interior 121 of the nut cap 120 has a tapering part 123 and a second locking member 122 that is axially separated from the tapering part 123. The second locking member is provided on a straight, non-tapering part of the nut cap 120. In the illustrated embodiment, the second locking member 122 is in the form of inner threads 122. The inner threads of the second locking member 122 of the nut cap 120 are adapted to integrate with the outer threads of the first locking member 114 of the holder 110. When the nut cap 120 is separated from the holder 110, i.e. when the second locking member 122 and the first locking member 114 are not engaged, the nut cap 120 is in an unlocked position. The unlocked position of the nut cap 120 enables movement of the steel wire 130 relative to the holder 110. The steel wire 130 can then be pushed further into the hollow interior 111 of the holder, or pulled out of the holder 110. When the steel wire 130 is pushed or pulled such that it is moved relative to the holder 110, the height of the ear cup 10 is adjusted relative to the head band 30 of the hearing protector unit 1.

When the nut cap 120 is screwed onto the holder 110 by engaging the threads of the locking members 114, 122 with each other, the tapering part 123 of the interior of the nut cap 120 comes into contact with the flanges 115a, 115b on the holder 110. When the nut cap 120 comes into contact with the flanges 115a, 115b, the nut cap 120 presses the flanges 115a, 115b radially towards the steel wire 130 that passes between the flanges 115a, 115b. The steel wire 130 will be clamped between the two flanges 115a, 115b. Due to the tapering shape of both the tapering part 123 in the nut cap 120 and the flanges 115a, 115b, the pressing of the flanges 115a, 115b towards the steel wire 130 will increase gradually along with the nut cap 120 being screwed onto the holder 110. Thereby, the force provided by the nut cap 120 pressing the holder 110 towards the steel wire 130 will continuously increase when the nut cap 120 is engaged with the holder 110. When the force increases, the friction between the holder 110, i.e. the flanges 115a, 115b, and the steel wire 130 increases. Eventually the friction will be of such amount that the steel wire 130 is locked relative to the holder 110. The nut cap 120 is thereby in a locking position, preventing a relative movement between the steel wire 130 and the holder 110.

Figure 3B:
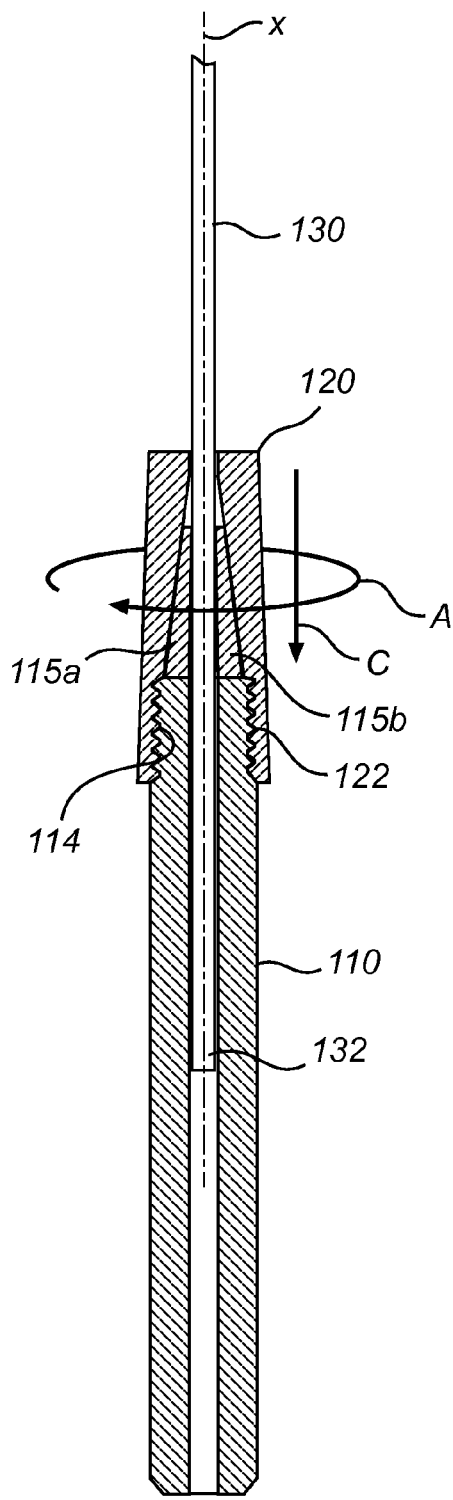
FIG. 3b is cross-sectional schematic side view of a height adjustment arrangement according to an embodiment of the invention.

FIG. 3b illustrates the engagement between the nut cap 120 and the holder 110 such that the steel wire 130 is clamped between the flanges 115a, 115b of the holder 110. When the steel wire 130 is clamped between the flanges 115a, 115b and the nut cap 120 has been screwed in a direction A onto the holder such that it is moved along a direction C and has reached the locking position, the steel wire 130 and the holder 110 is prevented from movement relative to each other. If the nut cap 120 is loosened from the locking position by turning it in a direction B (see FIG. 4), the pressing force on the flanges 115a, 115b will be decreased. When the pressing force is decreased, the steel wire 130 may be moved in any of the directions C or D (see FIG. 4) relative to the holder 110. Since the pressing force on the steel wire 130 is continuously adjustable, the force may be set to provide a friction force between the steel wire 130 and the holder 110 such that a user may override that friction force by pushing or pulling the steel wire 130 to adjust the height of the ear cup 10, and at the same time the friction force is large enough to hold the ear cup 10 in the set height position. The height adjustment arrangement 100 may thereby be used in the same way as prior art solutions, with the advantage that when wear of the parts in the arrangement decreases the friction force, the needed friction force may easily be reestablished by adjusting the engagement between the nut cap 120 and the holder 110.

Figure 4:
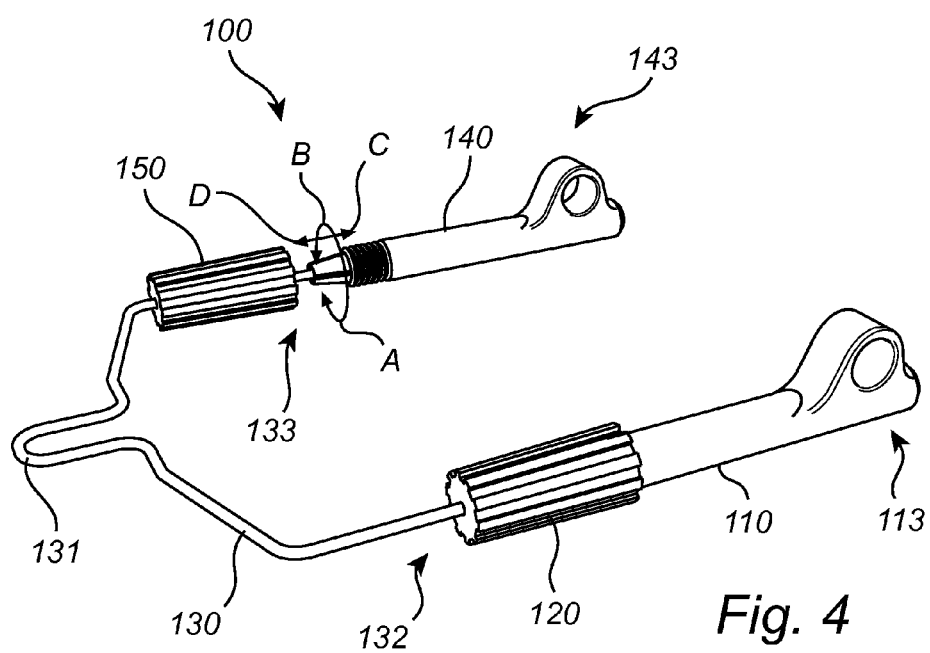
FIG. 4 is a perspective view of a height adjustment arrangement according to an embodiment of the invention.

FIG. 4 illustrates a height adjustment arrangement 100 for an ear cup 10 on a hearing protector unit 1, wherein a second holder 140 and a second nut cap 150 are arranged on the steel wire 130. A first end 131 of the steel wire 130 is adapted to be connected to the head band 30 on the hearing protector unit 1. The first holder 110 and the first nut cap 120 are arranged at the second end 132 of the steel wire 130. The second holder 140 and the second nut cap 150 are arranged at a third end 133 of the steel wire 130 in a similar way as the first holder 110 and first nut cap 120 at the second end 132. The first holder 110 and the second holder 140 are both adapted to be connected to respective sides of the same ear cup 10. One or both of the holders 110, 140 may be moved relative to the steel wire 130 when adjusting the height of the ear cup 10 by turning the first and the second nut caps 120, 150, such that the friction force between the holders 110, 140 and the steel wire 130 is decreased and the holders 110, 140 can be moved relative to the steel wire. The first holder 110 and the second holder 140 may, by means of the first nut cap 120 and the second nut cap 150, be fixed to the steel wire 130 at different heights.

In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. Height adjustment arrangement for an ear cup in a hearing protector unit, the height adjustment arrangement comprising:
    an elongated member adapted to be coupled in a first end to a head mounting portion of a hearing protector unit, and
    a tubular holding member connected to the elongated member, the tubular holding member being adapted to be coupled in a first end to an ear cup, wherein the tubular holding member provides a substantially hollow interior for receiving a second end of the elongated member, wherein a relative movement between the elongated member and the tubular holding member provides a height adjustment of an ear cup relative to a head mounting portion, and
    a clamping member, wherein the clamping member is arranged to be moved from an unlocked position, in which position relative movement between the elongated member and the tubular holding member is enabled, to a locking position, in which position relative movement between the elongated member and the tubular holding member is prevented, wherein the clamping member is adapted to, when in the locking position, be attached to the tubular holding member such that the clamping member presses a second end of the tubular holding member towards the elongated member to prevent relative movement between the elongated member and the tubular holding member, characterized in that
    the tubular holding member comprises a first locking member, wherein the second end of the tubular holding member is provided with two flanges tapering in a direction towards the clamping member and wherein the first locking member and the flanges are axially separated,
    the clamping member comprises a hollow interior with a tapering part which tapers in a direction away from the tubular holding member and a second locking member, wherein the tapering part and the second locking member are axially separated,
    wherein, when the clamping member is moved from the unlocked position to the locking position, the second locking member a is arranged to integrate with the first locking member and the tapering part is arranged to press the flanges towards the elongated member.

2. Height adjustment arrangement according to claim 1, wherein an amount of force with which the clamping member presses the second end of the tubular holding member towards the elongated member is adjustable.

3. Height adjustment arrangement according to claim 2, wherein the tubular holding member is provided with at least one slit at the second end of the tubular holding member.

4. Height adjustment arrangement according to claim 2, wherein the tubular holding member is provided with two slits at the second end of the tubular holding member.

5. Height adjustment arrangement according to claim 4, wherein the two slit provide the two flanges at the second end of the tubular holding member, and wherein the clamping member is adapted to, in the locking position, be attached to the tubular holding member such that the clamping member presses the two flanges at the second end of the tubular holding member towards the elongated member to prevent movement of the elongated member relative to the tubular holding member.

6. Height adjustment arrangement according to claim 2, wherein the clamping member is adapted to radially press the tubular holding member towards the elongated member.

7. Height adjustment arrangement according to claim 1, wherein the clamping member is arranged to, when moved from the unlocked position to the locking position, move along an axial direction of the elongated member.

8. Height adjustment arrangement according to claim 1, wherein the first locking member comprises outer threads on the tubular holding member and the second locking member comprises inner threads in an interior of the clamping member, wherein the outer and inner threads are adapted for threaded engagement with each other.

9. Height adjustment arrangement according to claim 8, wherein the pressing force by the clamping member on the second end of the tubular holding member towards the elongated member is adapted to increase along with an increased threaded engagement between the clamping member and the tubular holding member.

10. Height adjustment arrangement according to claim 1, wherein the first and second locking members together form a bayonet coupling.

11. A hearing protector, comprising:
    at least one ear cup;
    an elongated member;
    a head mounting portion attached to the at least one ear cup by the elongated member; and
    a height adjustment arrangement comprising:
        a tubular holding member having a hollow interior with tapering flanges, wherein the elongated member extends through the hollow interior of the tubular holding member; and
        a clamping member having a hollow interior with another tapering part that tapers in a direction complimentary to the tubular holding member flanges,
    wherein, in response to insertion of the tubular holding member into the clamping member, the flanges of the tubular holding member are pressed by clamping member towards the elongated member to secure the elongated member therein.

12. The hearing protector according to claim 11, wherein the tubular holding member and the clamping member comprise complimentary threading.

13. The hearing protector according to claim 11, wherein an amount of force with which the clamping member presses the tubular holding member towards the elongated member is adjustable.

14. The hearing protector according to claim 11, wherein the tubular holding member is provided with at least one slit.

15. The hearing protector according to claim 14, wherein the at least one slit forms the flanges at an end of the tubular holding member, and wherein the clamping member attaches to the tubular holding member such that the clamping member presses the flanges at the end of the tubular holding member towards the elongated member to prevent movement of the elongated member relative to the tubular holding member.

16. The hearing protector according to claim 15, wherein the clamping member radially presses the flanges of the tubular holding member towards the elongated member.

17. The hearing protector according to claim 11, wherein the clamping member moves from an unlocked position to a locking position by moving along an axial direction of the elongated member.

18. The hearing protector according to claim 11, wherein the tubular holding member comprises outer threads and the clamping member comprises complimentary inner threads.

19. A hearing protector, comprising:
    two ear cups;
    an elongated member joining the two ear cups together, the elongated member comprising wires; and
    a height adjustment arrangement that secures the wires to the two ear cups in an adjustable fashion, the height adjustment arrangement comprising:
        a tubular holding member having a hollow interior with tapering flanges,
    wherein at least one wire of the elongated member extends through the hollow interior of the tubular holding member; and
        a clamping member having a hollow interior with another tapering part that tapers in a direction complimentary to the tubular holding member flanges,
    wherein, in response to insertion of the tubular holding member into the clamping member, the flanges of the tubular holding member are pressed by clamping member towards the at least one wire of the elongated member to secure the elongated member therein.

* * * * *